US012728046B2

(12) United States Patent
Lipschutz et al.

(10) Patent No.: US 12,728,046 B2
(45) Date of Patent: Sep. 8, 2026

(54) SANITARY ARTICLE WITH SHAPING ELEMENT

(71) Applicant: Essity Hygiene and Health Aktiebolag, Gothenburg (SE)

(72) Inventors: Oscar Lipschutz, Gothenburg (SE); Louise Eliasson, Gothenburg (SE); Philip Blomström, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 377 days.

(21) Appl. No.: 18/256,598

(22) PCT Filed: Dec. 29, 2020

(86) PCT No.: PCT/EP2020/087970
§ 371 (c)(1),
(2) Date: Jun. 8, 2023

(87) PCT Pub. No.: WO2022/144071
PCT Pub. Date: Jul. 7, 2022

(65) Prior Publication Data

US 2023/0363957 A1 Nov. 16, 2023

(51) Int. Cl.
*A61F 13/47* (2006.01)
*A61F 13/476* (2006.01)
*A61F 13/56* (2006.01)

(52) U.S. Cl.
CPC ...... *A61F 13/4704* (2013.01); *A61F 13/5616* (2013.01); *A61F 2013/4708* (2013.01); *A61F 13/476* (2013.01)

(58) Field of Classification Search
CPC ................ A61F 13/4704; A61F 13/472; A61F 13/47236; A61F 13/47245; A61F 13/4756;

(Continued)

(56) References Cited

U.S. PATENT DOCUMENTS 3,595,237 A 7/1971 Sargent et al.
4,500,316 A 2/1985 Damico (Continued)

FOREIGN PATENT DOCUMENTS

CA 2339513 A1 9/2001
CN 1056048 A 11/1991

(Continued)

OTHER PUBLICATIONS

Brazil Application No. BR112023013018-2; Search Report dated Jun. 15, 2025; 4 pages.

(Continued)

*Primary Examiner* — Catharine L Anderson
(74) *Attorney, Agent, or Firm* — CANTOR COLBURN LLP

(57) ABSTRACT

Disclosed is a sanitary article, including a topsheet, a backsheet and absorbent core, the sanitary article having an extension in a longitudinal direction and transverse direction, first and second longitudinal edges extending in the longitudinal direction and front and rear transverse edges extending in the transverse direction, the sanitary article being divided in a front portion, crotch portion and rear portion, the absorbent core including a head portion, body portion and neck portion forming a transitional region between the head portion and body portion, the head portion being positioned in the front portion and the body portion being positioned in the crotch portion and rear portion, wherein the absorbent core in the front portion of the sanitary article is provided with a shaping element.

20 Claims, 5 Drawing Sheets

(58) Field of Classification Search
CPC .................. A61F 13/533; A61F 13/536; A61F 2013/4706; A61F 13/476
See application file for complete search history.

(56) References Cited

U.S. PATENT DOCUMENTS

| | | | |
|---|---|---|---|
| 5,201,727 | A | 4/1993 | Nakanishi et al. |
| 5,219,341 | A | 6/1993 | Serbiak et al. |
| 5,344,416 | A | 9/1994 | Niihara et al. |
| 5,401,268 | A | 3/1995 | Rodier |
| 5,429,630 | A | 7/1995 | Beal et al. |
| 5,462,166 | A | 10/1995 | Minton et al. |
| 5,484,636 | A | 1/1996 | Berg |
| 5,733,274 | A | 3/1998 | Osborn, III |
| 6,013,062 | A | 1/2000 | Dilnik |
| 6,293,932 | B1 | 9/2001 | Balzar et al. |
| 6,447,495 | B1 | 9/2002 | Luizzi et al. |
| 6,554,812 | B2 | 4/2003 | Drevik |
| 6,569,138 | B2 | 5/2003 | Helmfridsson et al. |
| 6,616,643 | B1 | 9/2003 | Costa |
| 6,746,435 | B1 | 6/2004 | Van Tilburg |
| 6,866,658 | B2 * | 3/2005 | Drevik .............. A61F 13/47245 604/385.31 |
| 6,945,967 | B2 | 9/2005 | Drevik et al. |
| 6,964,655 | B2 | 11/2005 | Killeen et al. |
| 7,059,474 | B2 | 6/2006 | Tippey |
| 7,078,583 | B2 | 7/2006 | Kudo et al. |
| 7,312,372 | B2 | 12/2007 | Miyama et al. |
| 7,727,213 | B2 * | 6/2010 | Nomoto .............. A61F 13/5376 604/385.101 |
| 7,922,706 | B2 * | 4/2011 | Konawa .............. A61F 13/4752 604/385.27 |
| 8,237,012 | B2 | 8/2012 | Miyama et al. |
| 8,986,273 | B2 | 3/2015 | Mercer |
| 8,993,832 | B2 | 3/2015 | Kuroda et al. |
| 9,114,044 | B2 | 8/2015 | Yoshiba |
| 9,173,786 | B2 | 11/2015 | Roh et al. |
| 9,566,196 | B2 | 2/2017 | Carlucci et al. |
| 9,775,752 | B2 | 10/2017 | Park et al. |
| 10,258,513 | B2 | 4/2019 | Kuramochi |
| 11,000,431 | B2 | 5/2021 | Blomström et al. |
| 11,058,591 | B2 | 7/2021 | Vohwinkel et al. |
| 11,065,161 | B2 | 7/2021 | Blomström |
| 11,246,770 | B2 | 2/2022 | Vohwinkel et al. |
| 11,357,672 | B2 | 6/2022 | Yonaha |
| 12,239,513 | B2 | 3/2025 | Schmoker et al. |
| 2003/0083637 | A1 | 5/2003 | Killeen et al. |
| 2003/0208177 | A1 | 11/2003 | D Alessio et al. |
| 2004/0138636 | A1 | 7/2004 | Cardin et al. |
| 2004/0243087 | A1 | 12/2004 | Kinoshita et al. |
| 2005/0283131 | A1 | 12/2005 | Zander et al. |
| 2006/0271003 | A1 | 11/2006 | Loescher |
| 2008/0312624 | A1 | 12/2008 | Hundorf et al. |
| 2009/0292268 | A1 | 11/2009 | Bagger-Sjöbäck et al. |
| 2011/0092944 | A1 | 4/2011 | Sagisaka et al. |
| 2012/0109093 | A1 | 5/2012 | Wilson et al. |
| 2012/0259306 | A1 | 10/2012 | Petersen |
| 2012/0316533 | A1 | 12/2012 | Norimoto |
| 2013/0123731 | A1 | 5/2013 | Mercer et al. |
| 2013/0310784 | A1 | 11/2013 | Bryant et al. |
| 2015/0018795 | A1 | 1/2015 | Park et al. |
| 2016/0235607 | A1 * | 8/2016 | Mercer .............. A61F 13/5644 |
| 2017/0354549 | A1 | 12/2017 | Cho et al. |
| 2018/0325750 | A1 | 11/2018 | Vohwinkel et al. |
| 2018/0325751 | A1 | 11/2018 | Vohwinkel et al. |
| 2018/0325753 | A1 | 11/2018 | Vohwinkel |
| 2018/0325754 | A1 | 11/2018 | Vohwinkel et al. |
| 2019/0374396 | A1 * | 12/2019 | Hood .................... A61F 13/532 |
| 2020/0129347 | A1 | 4/2020 | Blomström et al. |
| 2020/0138642 | A1 | 5/2020 | Wagner et al. |
| 2020/0138643 | A1 | 5/2020 | Hanson et al. |
| 2020/0138644 | A1 | 5/2020 | Hanson et al. |
| 2020/0155364 | A1 | 5/2020 | Rönnberg et al. |
| 2020/0155365 | A1 | 5/2020 | Blomström |
| 2020/0163809 | A1 | 5/2020 | Radne et al. |
| 2020/0281779 | A1 | 9/2020 | Kalentun |
| 2020/0368083 | A1 | 11/2020 | Rönnberg et al. |
| 2021/0220189 | A1 * | 7/2021 | Miao ................. A61F 13/53409 |
| 2022/0000683 | A1 | 1/2022 | Ekstedt et al. |
| 2022/0008261 | A1 | 1/2022 | Ekstedt et al. |
| 2023/0022804 | A1 | 1/2023 | Pollard |
| 2023/0240914 | A1 | 8/2023 | Blomström et al. |
| 2025/0213402 | A1 | 7/2025 | Dahl et al. |
| 2025/0381076 | A1 | 12/2025 | Sohl et al. |

FOREIGN PATENT DOCUMENTS

| | | | |
|---|---|---|---|
| CN | 1073090 | A | 6/1993 |
| CN | 1203520 | A | 12/1998 |
| CN | 1312060 | A | 9/2001 |
| CN | 1315168 | A | 10/2001 |
| CN | 1498608 | A | 5/2004 |
| CN | 1329010 | C | 8/2007 |
| CN | 101878011 | A | 11/2010 |
| CN | 101999964 | A | 4/2011 |
| CN | 203815725 | U | 9/2014 |
| CN | 203915242 | U | 11/2014 |
| CN | 204501249 | U | 7/2015 |
| CN | 105188626 | A | 12/2015 |
| CN | 105455962 | A | 4/2016 |
| CN | 106488760 | A | 3/2017 |
| CN | 206102848 | A | 4/2017 |
| CN | 106794099 | A | 5/2017 |
| CN | 107427402 | A | 12/2017 |
| CN | 110198694 | A | 9/2019 |
| CN | 110709043 | A | 1/2020 |
| CN | 110709044 | A | 1/2020 |
| CN | 110730651 | A | 1/2020 |
| CN | 110831555 | A | 2/2020 |
| CN | 110831556 | A | 2/2020 |
| CN | 110913814 | A | 3/2020 |
| CO | 5160278 | A1 | 5/2002 |
| CO | 2020000045 | A2 | 1/2020 |
| CO | 2020000057 | A2 | 1/2020 |
| CO | 2020000079 | A2 | 1/2020 |
| CO | 2021006995 | A2 | 6/2021 |
| CO | 2021007051 | A2 | 6/2021 |
| EP | 0471385 | A1 | 2/1992 |
| EP | 0549784 | A1 | 7/1993 |
| EP | 0674500 | A1 | 10/1995 |
| EP | 0983760 | A1 | 3/2000 |
| EP | 1138294 | A1 | 10/2001 |
| EP | 1208823 | A1 | 5/2002 |
| ES | 2230013 | T3 | 5/2005 |
| JP | H05506799 | A | 10/1993 |
| JP | H0586322 | U | 11/1993 |
| JP | H07506037 | A | 7/1995 |
| JP | H09253131 | A | 9/1997 |
| JP | 2009213719 | A | 9/2009 |
| JP | 2010227241 | A | 10/2010 |
| JP | 2011045608 | A | 3/2011 |
| JP | 2012213420 | A | 11/2012 |
| JP | 2013220225 | A | 10/2013 |
| JP | 2014150878 | A | 8/2014 |
| JP | 2014223216 | A | 12/2014 |
| JP | 2015100502 | A | 6/2015 |
| JP | 2016104089 | A | 6/2016 |
| JP | 2017006470 | A | 1/2017 |
| JP | 2017503624 | A | 2/2017 |
| JP | 2017176742 | A | 10/2017 |
| JP | 2019097898 | A | 6/2019 |
| JP | 2020526284 | A | 8/2020 |
| KR | 20050008509 | A | 1/2005 |
| RU | 2277891 | C2 | 6/2006 |
| WO | 9116873 | A1 | 11/1991 |
| WO | 9301781 | A1 | 2/1993 |
| WO | 9413236 | A1 | 6/1994 |
| WO | 9855063 | A1 | 12/1998 |
| WO | 0021477 | A1 | 4/2000 |
| WO | 0172254 | A2 | 10/2001 |
| WO | 2010110270 | A1 | 9/2010 |
| WO | 2013094779 | A1 | 6/2013 |
| WO | 2016068957 | A1 | 5/2016 |
| WO | 2018226132 | A1 | 12/2018 |

(56) References Cited

FOREIGN PATENT DOCUMENTS

| | | |
|---|---|---|
| WO | 2018226134 A1 | 12/2018 |
| WO | 2019007527 A1 | 1/2019 |
| WO | 2019007529 A1 | 1/2019 |
| WO | 2019008090 A1 | 1/2019 |
| WO | 2019008091 A1 | 1/2019 |
| WO | 2019039976 A1 | 2/2019 |
| WO | 2019112641 A1 | 6/2019 |
| WO | 2022144072 A1 | 7/2022 |
| WO | 2022144073 A1 | 7/2022 |

OTHER PUBLICATIONS

Brazil Application No. BR112023012912-5; Search Report dated Jun. 15, 2025; 4 pages.
Chinese Application No. 202080108282.0; Office Action with English translation dated Aug. 27, 2024; 21 pages.
International Search Report & Written Opinion for International Application No. PCT/EP2020/087970; International Filing Date: Dec. 29, 2020; Date of Mailing: Sep. 17, 2021; 13 pages.
International Search Report & Written Opinion for International Application No. PCT/EP2020/087972; International Filing Date: Dec. 29, 2020; Date of Mailing: Sep. 24, 2021; 13 pages.
International Search Report & Written Opinion for International Application No. PCT/EP2020/087973; International Filing Date: Dec. 29, 2020; Date of Mailing: Oct. 7, 2021; 11 pages.
Non-Final Office Action issued in U.S. Appl. No. 18/256,623 dated Mar. 21, 2024.
Chinese Application No. 202080108180.9; Office Action with English translation dated Aug. 28, 2024; 14 pages.
Advisory Action issued in U.S. Appl. No. 18/256,523 dated Feb. 13, 2024; 6 pages.
Final Office Action issued U.S. Appl. No. 18/256,523 dated May 2, 2024.
Non-Final Office Action issued in U.S. Appl. No. 18/256,523 dated Mar. 21, 2024.
Non-Final Office Action issued in U.S. Appl. No. 18/256,523 dated Nov. 9, 2023; 23 pages.
Chinese Application No. 202080107950.8; Office Action with English translation dated Dec. 27, 2024; 16 pages.
Chinese Application No. 202080107950.8; Office Action with English translation dated Aug. 28, 2024; 17 pages.
U.S. Appl. No. 18/256,505; Non-Final Office Action dated Aug. 27, 2025; 61 pages.
Chinese Application No. 202080107950.8; Office Action with English translation dated May 22, 2025; 19 pages.
U.S. Final Office Action for U.S. Appl. No. 16/626,672; Application Filing Date Dec. 26, 2019; Report Mail Date Nov. 20, 2023 (30 Pages).
Australian Government, IP Australia, Office Action issued in AU Application No. 2017422549, dated Apr. 21, 2020 (4 pages).
Chinese Application No. 201980102566.6; Office Action dated Aug. 3, 2022; 14 pages.
Chinese Application No. 201980102571.7; Office Action dated Aug. 8, 2022; 19 pages.
Colombia Office Action for Columbian Application No. NC2022/0008163; Report Mail Date Jul. 24, 2024 (30 Pages; with English Translation).
Colombia Patent Application No. NC2023/0008638; Office Action with English translation dated Oct. 10, 2025; 23 pages.
Colombian Patent Office, Office Action issued in CO application No. NC2020/0000068 dated Jul. 16, 2021 with English explanation of rejections/relevance from local counsel (11 pages).
Colombian Patent Office, Office Action issued in CO application No. NC2020/0000068 dated Nov. 30, 2021 (10 pages).
Columbian Office Action, Application No. PCT/EP2020/087973, mailed Nov. 20, 2025; with English Translation, 28 pages.
Columbian Office Action, International Application No. PCT/EP2020/087970, mailed Dec. 4, 2025; with English Translation, 22 pages.
Egypt Office Action, Application No. 2023050817, mailed Oct. 2025, with English Translation, 22 pages.
Final Offie Action issued in U.S. Appl. No. 16/626,672 dated Jul. 11, 2024.
International Preliminary Report on Patentability for International Application No. PCT/EP2017/067068, dated Oct. 25, 2019, 18 pages.
International Preliminary Report on Patentability for International Application No. PCT/EP2017/067071, dated Oct. 25, 2019, 21 pages.
International Preliminary Report on Patentability for International Application No. PCT/EP2018/068232, dated Oct. 23, 2019, 21 pages.
International Preliminary Report on Patentability for International Application No. PCT/EP2018/068233, dated Oct. 21, 2019, 16 pages.
International Search Report & Written Opinion for International Application No. PCT/EP2022/058785; International Filing Date: Apr. 1, 2022; Date of Mailing: Nov. 18, 2022; 10 pages.
International Search Report & Written Opinion for International Application No. PCT/EP2022/069219; International Filing Date: Jul. 11, 2022; Date of Mailing: Feb. 6, 2023; 9 pages.
International Search Report and Written Opinion for International Application No. PCT/EP2017/067068, dated Jan. 8, 2018, 15 pages.
International Search Report and Written Opinion for International Application No. PCT/EP2017/067071, dated Jan. 8, 2018, 20 pages.
International Search Report and Written Opinion for International Application No. PCT/EP2018/068232, dated Aug. 16, 2018, 17 pages.
International Search Report and Written Opinion for International Application No. PCT/EP2018/068233, dated Aug. 17, 2018, 17 pages.
International Serach Report & Written Opinion for International Application No. PCT/SE2019/051281; International Filing Date: Dec. 13, 2019; Date of Mailing: Jul. 20, 2020; 15 pages.
International Serach Report & Written Opinion for International Application No. PCT/SE2019/051282; International Filing Date: Dec. 13, 2019; Date of Mailing: Jul. 20, 2020; 13 pages.
Japanese Patent Office, Office Action issued in JP 2020-500043 dated Mar. 31, 2021 with English translation, 17 pages.
Japanese Patent Office, Office Action issued in JP 2020-500129 dated Mar. 31, 2021 with English translation, 18 pages.
Japanese Patent Office, Office Action issued in JP Application No. 2020-500068, dated Feb. 2, 2021 with partial English Translation (14 pages).
Japanese Patent Office, Office Action issued in JP Application No. 2020-500117, dated Feb. 1, 2021 with partial English Translation, 14 pages.
Malaysian Application No. PI2020000003; Malaysian Search Report dated May 27, 2022; 2 pages.
Merriam-Webster Dictionary, "Upside Down Definition & Meaning" https://www.merriam-webster.com/dictionary/upside%down (Year 2023).
National Intellectual Property Administration (CNIPA) of the People's Republic of China, First Office Action issued in CN Application No. 20170092879.9, dated Mar. 17, 2021 with English translation, 24 pages.
National Intellectual Property Administration (CNIPA) of the People's Republic of China, First Office Action, Application No. 201880044787.8, dated Apr. 20, 2020 and English Translation (13 pages).
National Intellectual Property Administration (CNIPA) of the People's Republic of China, Office Action issued in CN 201780092880.1 dated Mar. 29, 2021 with English Translation, 20 pages.
Non-Final Office Action issued in U.S. Appl. No. 17/783,943, dated Feb. 16, 2024 (22 Pages).
Office Action issued in Colombia Application No. NC2022/0008157 dated May 8, 2024.
Russian Patent Office, Decision to Grant issued in RU application No. 2019139865/(078371), dated Jul. 7, 2020 with English translation (21 pages).

(56) References Cited

OTHER PUBLICATIONS

Russian Patent Office, Decision to Grant issued in RU Application No. 219139870/03(078379), dated Jun. 25, 2020 with English Translation (22 pages).
U.S. Final Office Action for U.S. Appl. No. 17/783,943; Application Filing Date Jun. 9, 2022; Report Mail Date Aug. 7, 2023 (pp. 1-15).
U.S. Non-Final Office Action for U.S. Appl. No. 17/783,943; Application Filing Date Jun. 9, 2022; Report Mail Date Jun. 1, 2023 (pp. 1-16).
U.S. Office Action for U.S. Appl. No. 16/626,039; Application Filing Date Dec. 23, 2019; Report Mail Date Aug. 3, 2023 (pp. 1-19).
U.S. Office Action for U.S. Appl. No. 16/626,672; Application Filing Date Dec. 26, 2019; Report Mail Date Jul. 27, 2023 (pp. 1-21).
U.S. Appl. No. 17/783,533, filed Jun. 8, 2022, Non-Final Office Action mailed Jan. 16, 2025, 16 pages.
U.S. Appl. No. 18/256,505, filed Jun. 8, 2023, Final Office Action mailed Dec. 19, 2025; 22 pages.

* cited by examiner

SANITARY ARTICLE WITH SHAPING ELEMENT

CROSS REFERENCE TO RELATED APPLICATIONS

This application is a National Stage application of PCT/EP2020/087970, filed Dec. 29, 2020, which is incorporated by reference in its entirety herein.

TECHNICAL FIELD

The present disclosure relates to a sanitary article with first and second fastening wings, the sanitary article comprising a shaping element.

BACKGROUND OF THE INVENTION

Sanitary articles to which this disclosure relates are typically intended to absorb body liquids, such as urine and blood. Users place high demands on such articles, requiring them to be thin, comfortable and at the same time effectively absorb body liquids.

Disposable sanitary articles, such as sanitary napkins, pantyliners or the like typically include a liquid pervious topsheet, intended to face the wearer during use, a liquid impervious backsheet and an absorbent structure there between. Such absorbent structures may be relatively thin and compressed. Absorbent structures that are relatively compressed may lack flexibility and it is important to ensure that these relatively thin and compressed articles absorb liquid quickly, do not leak and are comfortable to wear. For attachment to the user garment, the sanitary article may include first and second fastening wings, which are intended to be folded around the user garment and adhesively attached thereto. The fastening wings provide a lateral outwardly stretching of the sanitary article which also may have an impact on the fit of the sanitary article. For feminine sanitary napkins the fit, both in the front, crotch and rear portions, is important for preventing leakage but also for the sanitary article to be discreet and comfortable during use.

It is furthermore of importance that the sanitary article gives the user a visual perception of leakage security and good fit, enabling the user to feel secure and thereby enhancing the well-being of the user.

Consequently, there is a need for a sanitary article provided with fastening wings having a good fit and an enhanced leakage security and which is discreet and comfortable to wear and has an enhanced visual appearance.

SUMMARY OF THE INVENTION

One or more of the above objects is achieved with a sanitary article according to claim 1. Further advantages and advantageous features of the present invention are disclosed in the following description and in the dependent claims.

As set out herein, the present disclosure relates to a sanitary article, such as a sanitary napkin or a pantiliner, the sanitary article comprising a topsheet, a backsheet and an absorbent core arranged between the topsheet and the backsheet. The sanitary article has an extension in a longitudinal direction and in a transverse direction. The sanitary article has first and second longitudinal side edges extending in the longitudinal direction and front and rear transverse side edges extending in the transverse direction. The sanitary article is made up of a front portion, a crotch portion and a rear portion, as seen in the longitudinal direction. The absorbent core comprises a head portion, a body portion and a neck portion, the neck portion forming a transitional region between the head portion and the body portion. The head portion is positioned in the front portion of the sanitary article and the body portion is positioned in the crotch portion and in the rear portion of the sanitary article. A transverse width $W_n$ of the absorbent core at the neck portion is smaller than a maximum transverse width of the absorbent core in the head portion and in the body portion. The absorbent core in the front portion of the sanitary article is provided with a shaping element, such as a compressed groove, a channel, or a low-density region, promoting folding or shaping of the sanitary article. The shaping element comprises a rearmost point, as seen in the longitudinal direction of the sanitary article. The sanitary article has a first fastening wing extending along the first longitudinal side edge between a first wing front junction and a first wing rear junction and a second fastening wing extending along the second longitudinal side edge between a second wing front junction and a second wing rear junction. The first fastening wing has a first adhesive region on a garment facing side thereof and the second fastening wing has a second adhesive region on a garment facing side thereof. Each of the first and the second adhesive regions has a respective frontmost border, as seen in the longitudinal direction, wherein in a flat unfolded configuration of the sanitary article with the first and second fastening wings being unfolded and extending outwardly of a respective side of the absorbent core, the rearmost point of the shaping element is arranged in an area of the absorbent core extending between a transverse extension of the frontmost border of the first and/or the second adhesive region, as seen in the longitudinal direction, and to the maximum transverse width of the head portion.

The term "sanitary article" refers to a product that is placed against the skin of the wearer in the wearer's crotch to absorb and contain body exudates, such as urine, feces and menstrual fluid. The disclosure mainly refers to disposable sanitary articles, which means articles that are not intended to be laundered or otherwise restored or reused as a sanitary article. Examples of disposable sanitary articles include feminine hygiene products such as sanitary napkins, panty liners, incontinence pads and the like.

Sanitary articles provided with fastening wings will, upon folding of the fastening wings and fastening to the underwear of the user, be subjected to lateral restricting forces which affect the folding and shaping of the sanitary article upon use by the wearer. The sanitary article is provided with a shaping element in the front portion of the sanitary article interacting with the neck and head portion of the sanitary article to promote bending in a transversal direction of the front portion to enhance the fit of the sanitary article front portion.

Since the absorbent core according to the present disclosure has a neck region arranged at the groin area of the user where compressive forces are received from a lateral direction, the provision of a neck region retains the flat shape of the absorbent core in this area and reduces twists or wrinkles which may otherwise occur, and the sanitary article will better be held in its position during use. Such configuration furthermore means that the article can bend more easily in a transversal direction at the neck portion.

The maximum width of the head portion is measured between a first and a second point along a respective longitudinal side edge of the absorbent core and an imaginary maximum head portion transition line may be drawn between these points to define the frontmost border of the area in which the rearmost point of the shaping element is arranged.

According to the present disclosure, the rearmost point of the shaping element is arranged in an area of the absorbent core extending between a transverse extension of the frontmost border of the first and/or the second adhesive region, as seen in the longitudinal direction, and the maximum width of the head portion. This promotes bending of the front portion and the core head portion towards the user in an area not laterally restricted by the adhesion between fastening wings and the undergarment. This means that the front portion covers the pubic regions of the wearer better while the crotch portion is positioned close to the crotch area of a wearer.

The transverse width of the absorbent core at the neck region may be smaller than any transverse width of the head portion of the absorbent core, the width being measured along longitudinal side edges of the absorbent core and does not include configurations of the core in which the head portion is rounded at a front edge of the absorbent core. The transverse width of the neck region may be smaller than any transverse width of the body portion of the absorbent core, the width being measured along longitudinal side edges of the absorbent core and does not include configurations of the core in which the body portion of the is rounded at a rear edge of the absorbent core.

The front portion, crotch portion and rear portion may be of equal length as seen in the longitudinal direction. Alternatively, the front and the rear portion may constitute 30% each, as seen in the longitudinal direction, of the length of the sanitary article and the crotch portion may constitute 40% of the length of the sanitary article, as seen in the longitudinal direction. If for example the sanitary article is a night product, the rear portion and the crotch portion may each constitute 40% of the length of the sanitary article and the front portion may constitute 20% of the length of the sanitary article. The measurement is made from the frontmost and to the rearmost point of the sanitary article and is measured in the longitudinal direction.

A portion of the shaping element may coincide with the neck portion of the absorbent core, as seen in the longitudinal direction, or may be arranged not more than 30 mm from the neck portion, or not more than 15 mm from the neck portion, as measured in the longitudinal direction. Such configuration implies that the article bends more easily at the neck portion in a transversal direction. Therefore, the front portion and the head portion can bend towards the user and the front portion can better cover the pubic regions of the wearer while the crotch portion is able to be positioned close to the crotch area of a wearer.

The first wing front junction and/or the second wing front junction may be aligned with the neck portion of the absorbent core, as seen in the longitudinal direction, or may be arranged not more than 30 mm rearwardly, or not more than 15 mm rearwardly, from the neck portion as measured in the longitudinal direction. This configuration further enhances an advantageous shaping of the front portion of the sanitary article promoting a facilitated upwards transverse folding of the sanitary article in this region following the anatomy of the wearer while the crotch portion of the sanitary article remains flat and close to the crotch region of the wearer.

The shaping element may have a V-shaped section pointing towards the transverse front edge of the sanitary article and/or a V-shaped section pointing towards the transverse rear edge of the sanitary article. The shaping element may alternatively or additionally have a first and a second compressed or low-density region arranged along a respective first and second longitudinal edge region of the absorbent core at the neck portion. Such shaping element may further accentuate the neck portion of the absorbent core and promote bending and shaping of the absorbent core in a well-controlled manner.

The shaping element may be a compressed groove or a channel with a depth corresponding to 50% or more of a no-load thickness of the absorbent core, as measured in comparison with an area of the absorbent core being adjacent to the shaping element, such as from 50% to 100% of the no-load thickness of the absorbent core, or a depth corresponding to 65% or more, or 75% or more of a no-load thickness of the absorbent core. The shaping element may alternatively be a low-density region in which the low-density region has a density corresponding to 50% or less of the density of the absorbent core, in comparison with an area of the absorbent core being adjacent to the shaping element, or 35% or less, 25% or less of the density of the absorbent core. The no-load thickness or the density of the absorbent core thus being measured in comparison with an area of the absorbent core being adjacent to the shaping element.

If the shaping element is provided by embossing, i.e. a compressed shaping element, the topsheet may optionally be embossed together with the absorbent core.

The shaping element may extend to a first and a second longitudinal edge region of the absorbent core. When the shaping element extends to a first and a second longitudinal edge region of the absorbent core, a well-controlled and improved bending of the absorbent core may be achieved.

The shaping element may be symmetrical about a longitudinal centerline of the absorbent core. For a shaping element intended to conform the absorbent core to the user anatomy, a shaping element being symmetrical about a longitudinal centerline of the absorbent core is advantageous for providing a symmetric bending of the sanitary article.

The first and second fastening wings may be asymmetrical with respect to any transverse axis extending in the transverse direction, for example such that the widest section of the fastening wings are displaced with respect to each other and thereby are not facing each other.

The first and second fastening wings may be asymmetrical with respect to each other as seen along any longitudinal axis extending in the longitudinal direction.

Asymmetry of the fastening wings with respect to any transverse axis extending in the transverse direction and with respect to each other as seen along any longitudinal axis extending in the longitudinal direction may enable wider fastening wings since the wings may be fastened in an overlapping manner, as seen in the longitudinal direction, and without overlayer each other and thus sticking to each other. Consequently, an enhanced fastening may be provided, resulting in an enhanced fit. However, to provide an improved symmetrical folding of the front portion of the sanitary article, the frontmost point of the first and/or second adhesive regions may be arranged along a common transverse extension.

Each of the first and the second adhesive regions may have a respective portion with a greater width and a respective portion with a smaller width, as measured in the transverse direction. The adhesive portions with the wider widths may coincide with a portion of the respective fastening wing having a wider width and the adhesive portions with the smaller width may coincide with a portion of the respective fastening wing having a smaller width, as seen in the longitudinal direction. This promotes a secure fastening and fit of the sanitary article.

The first and the second adhesive region may be reverse mirror images of each other.

A frontmost point of the shaping element may be aligned with the neck portion of the absorbent core. Consequently, folding at the neck portion of the absorbent core is facilitated and bending in a well-controlled manner is promoted.

The body portion of the absorbent core in the rear portion of the sanitary article may be divided along a longitudinal centerline of the absorbent core into a first core leg portion and a second core leg portion. Since the absorbent article is divided along a longitudinal centerline of the absorbent core into a first core leg portion and a second core leg portion, the core may fold between the buttocks of the user and provide, in combination with the arrangement of the shaping element according to the present disclosure, a sanitary napkin which adapts to the wearer anatomy in the front portion, crotch portion and in the rear portion of the sanitary article.

The absorbent core may be provided with a central low-density area, the central low-density area being arranged in the crotch portion of the sanitary article. The absorbent core may be compressed, such as by embossing or calendaring around the low-density area. The absorbent area may alternatively be provided with an opening being arranged in the crotch portion of the sanitary article. The absorbent core may comprise a first and second core layer, wherein the opening is provided in the first core layer. The first core layer may be arranged between the topsheet and the second core layer. Such absorbent core may provide a quick liquid intake and spreading, which may be of particular advantage for a close fitting sanitary article.

The absorbent core may be provided with a rear shaping element comprising a first leg section and a second leg section, the first and the second leg sections converging towards a longitudinal centerline of the absorbent core and pointing towards the transverse rear edge of the sanitary article, each of the first and the second leg sections having a respective first and second frontmost end point and wherein each of the first and the second frontmost end points of the respective first and second leg sections is aligned with or arranged rearwardly of a first and second rearmost border of the first and the second adhesive regions. The rear shaping element is an embossed rear shaping element, a low-density rear shaping element or a channel

BRIEF DESCRIPTION OF THE DRAWINGS

The present invention will be further explained hereinafter by means of non-limiting examples and with reference to the appended drawings wherein.

DETAILED DESCRIPTION

Figure 1:
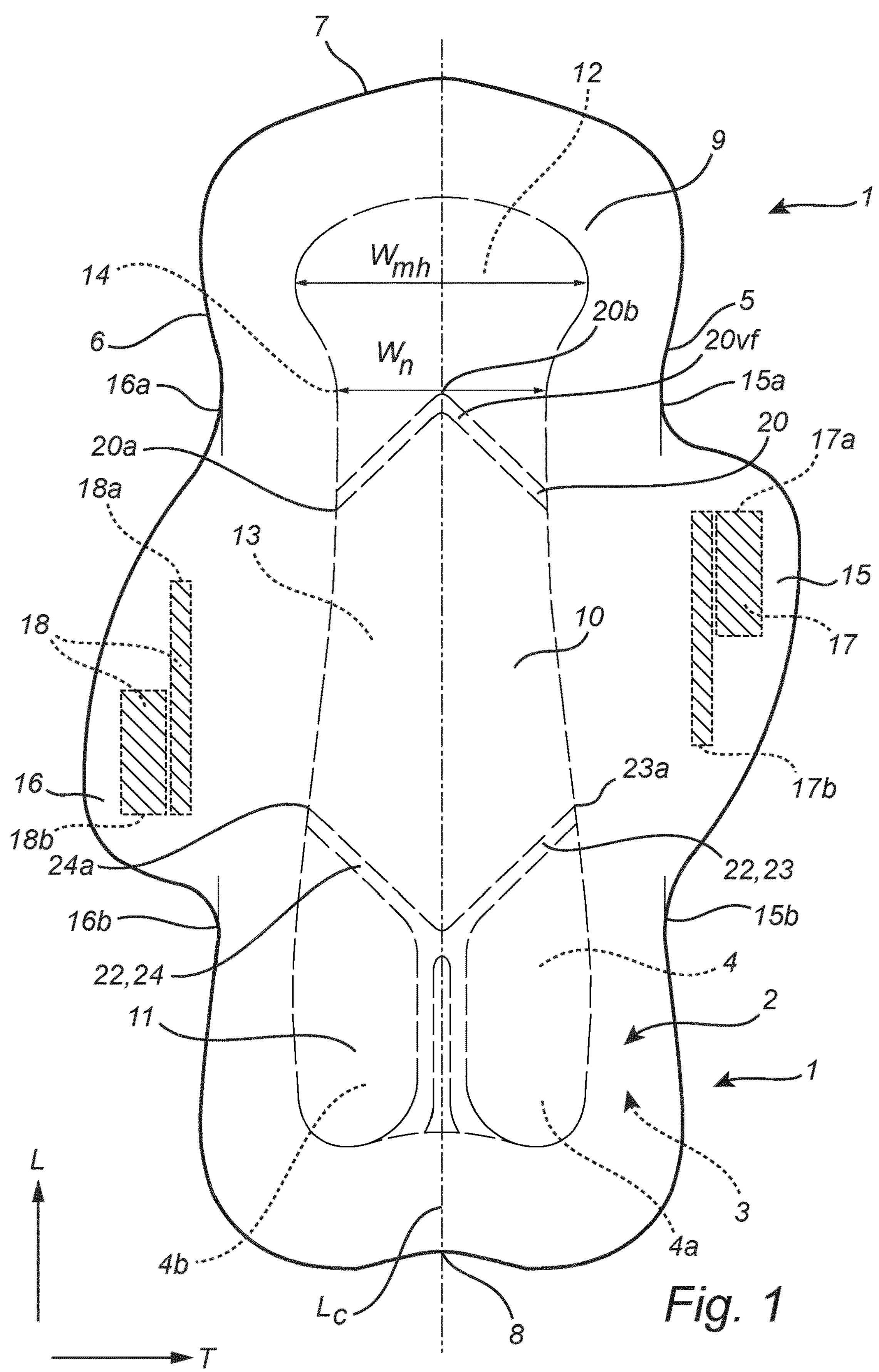
FIG. 1 illustrates a sanitary article according to the present disclosure.

It is to be understood that the drawings are schematic and that individual components are not necessarily drawn to scale. The sanitary articles shown in the drawings are provided as examples only and should not be considered limiting to the invention. Accordingly, the scope of invention is determined solely by the scope of the appended claims.

FIG. 1 illustrates a sanitary article 1 according to the present disclosure. The sanitary article comprises a topsheet 2, a backsheet 3 and an absorbent core 4 arranged between the topsheet 2 and the backsheet 3.

The topsheet 2 may include or consist of fibrous nonwoven layer(s) being spunbonded, meltblown, carded, hydroentangled, wetlaid. Suitable nonwoven materials can be composed of natural fibers, such as woodpulp or cotton fibers, synthetic thermoplastic fibers, such as polyolefins, polyesters, polyamides and blends and combinations thereof or from mixtures of natural and synthetic fibers. The materials suited as topshet material should be soft and non-irritating to the skin and be readily penetrated by body fluid, such as menstrual fluid and urine.

The backsheet 3 may consist of a thin plastic film, e.g. a polyethylene or polypropylene film, a nonwoven material coated with a liquid impervious material, a hydrophobic nonwoven, which resist liquid penetration. Laminates of plastic films and nonwoven materials may also be used. The backsheet material can be breathable to allow vapor to escape from the absorbent structure, while still preventing liquids from passing through the backsheet material.

The absorbent core 4 constitutes the absorbent structure of the article which acquires and stores bodily fluids. The absorbent core may be of any conventional kind. Examples of commonly occurring absorbent materials are cellulosic fluff pulp, tissue, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form suitable for use in absorbent composites including particles, fibres, flakes, spheres, and the like. A high absorption capacity is provided by the use of high amounts of superabsorbent material. Thin absorbent cores which are common in for example sanitary napkins, baby diapers and incontinence guards, often comprise a compressed, mixed or layered structure of cellulosic fluff pulp and superabsorbent polymers. The size and absorbent capacity of the absorbent core may be varied to suit different product types, such as sanitary napkins for adult incontinent persons or panty liners.

Generally, the core can be of unitary construction, whereby for example the manufacturing process can be simplified. The phrase "unitary construction" in the present context is intended to mean that the absorbent core is constructed from essentially one type of material, this being essentially the same material, or essentially the same combination of two or more materials throughout the absorbent core. Variations in density and concentration of the material may occur, but these are limited to those which may be obtained without incorporation of regions which have been formed separately and then physically joined to each other. For example, when the absorbent core comprises a matrix of hydrophilic fibres and superabsorbent material as described above, the relative concentrations of superabsorbent material and fibres may be different in different parts of the core. However, the absorbent core of unitary construction does not comprise layers or laminates of different composition. Likewise, variations in the density or concentration of various components across the longitudinal direction, the transverse direction or the thickness direction of the absorbent core are acceptable, yet the core should not comprise areas or layers of different composition which are formed separately and later joined together.

A suitable technique for manufacturing the absorbent cores of the present disclosure is mat-forming through an air-laying process. In the process an air-permeable mould is provided. Fibrous material is air-laid into the mould and the mould is filled, whereby an absorbent core is produced in with a desired amount of fibrous material.

The sanitary article 1 may furthermore comprise an acquisition layer (not shown in the figure) arranged between the absorbent core 4 and the topsheet 2. The acquisition layer is suitably placed on top of the absorbent core. The liquid acquisition sheet is adapted to quickly receive and temporarily store discharged liquid before it is absorbed by the absorbent core 4. Such acquisition distribution layers may be composed of for example airlaid nonwoven, spunlace nonwoven, high loft nonwoven or foam materials. The nonwoven material may be hydrophilic. A hydrophilic material may be obtained by adding a surfactant.

An air laid nonwoven can be produced with fluff, wood pulp, and here the fluff fibres are dispersed into a fast-moving air stream and condensed onto a moving screen by means of pressure and vacuum. The web can be bonded with resin and/or thermal plastic resin dispersed within the pulp. The web can be thermobonded (by heat), latex bonded (with adhesive) or multibonded (a combination of thermo and latex bonding) or mechanically bonded (high compression and temperature, bonding by hydrogen). The grammage of the airlaid nonwoven can suitably be from 50 to 100 gsm.

A high loft material is a nonwoven material and may be substantially free from absorbing fibres and superabsorbent material. The high loft nonwoven material may comprise thermoplastic polymer fibres, and may be selected from but not limited to, polyesters, polyamides and polyolefins such as polyethylenes (PE) and polypropylenes (PP), and may be a mixture of any of these. The high loft material refers to low-density bulky fabrics, as compared to flat, paper-like fabrics. High loft webs are characterised by a relatively low density. This means that there is a relatively high amount of void space between the fibres. The high loft nonwoven fibrous layer of the invention may typically have a density below 0.200 g/cc (200 kg/$m^3$), in particular ranging from 0.015 g/cc to 0.150 g/cc (15 kg/$m^3$ to 150 kg/$m^3$), in particular from 0.030 g/cc to 0.100 g/cc (30 to 100 kg/$m^3$), for example 0.065 g/cc (65 kg/$m^3$). The average density can be calculated by dividing the basis weight of the high loft layer by its thickness measured at a pressure of 0.5 kPa (see the method details further below). Normally the thickness of high loft materials is more than about 0.5 mm, such as more than 1 mm or suitably 1.5-2.0 mm, and the solid content is low, usually less than 15% by volume. The high loft nonwoven layer may advantageously be a spunmelt nonwoven. Spunmelt is a generic term describing the manufacturing of nonwoven webs directly from thermoplastic polymers. It encompasses two processes and the combination of both: spunlaid (also known as spunbond) nonwoven and meltblown nonwoven. In a spunlaid process, polymer granules are melted and molten polymer is extruded through spinnerets. The continuous filaments are cooled and deposited on to a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web. The liquid acquisition sheet material may be of a spunbonded material and may be a spunbond- meltbond-spunbond (SMS) material. The high loft nonwoven layer may in particular have a thickness ranging from 0.30 mm to 2.00 mm, for example 1.0 mm as measured at a pressure of 0.5 kPa (according to the test method referred to in PCT Application No. PCT/SE2017/050612). The grammage, i.e. basis weight of the high loft material may for example range from 15 gsm to 500 gsm, in particular from 30 gsm to 200 gsm, such as 30-90 gsm, for example 64 gsm.

According to a further variant, the liquid acquisition sheet is a spunlace, also referred to as spunbond, nonwoven material. A spunlace nonwoven product is derived from a process of entangling a web of loose fibres through multiple rows of jets of water at high pressure; this process entangles the fabrics and interlinks the fibres. There are several terms for spunlace nonwoven fabric or spunlaced, such as jet entangled, needled, hydroenentangled or hydraulic, but the term spunlace or spunlaced is the most popular in the nonwoven industry. The raw material for the acquisition sheet can be polypropylene (PP), polyethylene (PE) polyester (PET), polyamide (PA), cellulosic fibres or a combination of these and different weights and compositions are possible, such as viscose, polyester, cotton, nylon and microfibre, wherein viscose is the most commonly used raw material. Thus, if a combination of different fibres is used, this can be a mixture of fibres from different polymers, although each fibre can also include different polymers (e.g. PP/PE bi-component fibres or PP/PE copolymers). Where appropriate, the plastic film can consist of PE or PP, PET, PLA or amyl (or, for that matter, any other thermoplastic polymer), or a mixture or copolymers of the aforementioned polymers. The spunlace material usually comprises polypropylene or polyethylene fibres which provide for optimal comfort for the nonwoven material. Other suitable fibres for making the nonwoven material are for example natural fibres such as bamboo, cotton and flax. The grammage of the spunlace nonwoven material can be typically from 30-80 gsm.

The sanitary article 1 has an extension in a longitudinal direction L and in a transverse direction T. The sanitary article 1 is delimited by first and second longitudinal side edges 5,6 extending in the longitudinal direction L and front and rear transverse side edges 7,8 extending in the transverse direction T. The sanitary article comprises a front portion 9, a crotch portion 10 and a rear portion 11, as seen in the longitudinal direction L. The absorbent core 4 comprises a head portion 12, a body portion 13 and a neck portion 14, the neck portion 14 forming a transitional region between the head portion 12 and the body portion 13. The head portion is positioned in the front portion 9 of the sanitary article 1 and the body portion 13 is positioned in the crotch portion 10 and in the rear portion 11 of the sanitary article 1. A transverse width $W_n$ of the absorbent core 4 at the neck portion 14 is smaller than a maximum transverse width $W_{mh}$ of the absorbent core 4 in the head portion 12 and in the body portion 13. The transverse width of the absorbent core 4 at the neck region is smaller than any transverse width of the head portion 12 of the absorbent core 4, the width being measured along the longitudinal side edges 5,6 of the absorbent core 4 and does not include measurements of points at any rounded front edge of the absorbent core 4.

The absorbent core 4 is provided with a shaping element 20 in the front portion 9 of the sanitary article 1. The shaping element may be a compressed groove, channel, or a low-density region, promoting folding or shaping of the sanitary article 1. The shaping element is not constituted by a folding line of the sanitary article achieved during tri-folding of the sanitary article. In FIG. 1 the shaping element 20 is a V-shaped embossing with a tip pointing towards the front edge 7 of the sanitary article 1 and comprises a rearmost point 20*a* as seen in the longitudinal direction L of the sanitary article 1. In FIG. 1 the rearmost endpoint 20*a* is the respective endpoints of the legs of the V-shaped embossing. In FIG. 1 the topsheet 2 is embossed together with the absorbent core 4. The V-shaped embossing may be a continuous embossed line or be dotted or dashed embossed line. The shaping element may alternatively be a low-density region, in which region the absorbent core 4 has a lower density than an adjacent part of the absorbent core 4. The low-density region may for example have a density being at least 50% lower than an adjacent region, of the absorbent core 4 or a density being at least 65% lower than an adjacent region of the absorbent core 4, optionally between 50% and 85% lower than an adjacent region of the absorbent core 4. The shaping element may alternatively be a channel provided in the absorbent core, wherein the absorbent core 4 is free from absorbent material without being compressed. The absorbent core may comprise a first and a second core layer, wherein the channel may extend completely through one of the core layers.

The sanitary article 1 has a first fastening wing 15 extending along the first longitudinal side edge 5 between a first wing front junction 15*a* and a first wing rear junction 15*b* and a second fastening wing 16 extending along the second longitudinal side edge 6 between a second wing front junction 16*a* and a second wing rear junction 16*b*. The first wing front junction 15*a* and the second wing front junction 16*a* is arranged with a distance d (see FIG. 5) of not more than 30 mm rearwardly, or not more than 15 mm rearwardly, from the neck portion as measured in the longitudinal direction L. Alternatively, the front wing junction 15*a* and/or the second wing front junction 16*a* may be aligned with the neck portion 14 of the absorbent core 4, as seen in the longitudinal direction L.

The first and second fastening wings 15,16 of the sanitary article 1 according to FIG. 1 are asymmetrical with respect to any transverse axis extending in the transverse direction T and with respect to each other as seen along any longitudinal axis extending in the longitudinal direction L.

The first fastening wing 15 has a first adhesive region 17 on a garment facing side thereof and the second fastening wing 16 has a second adhesive region 18 on a garment facing side thereof. Each of the first and the second adhesive regions 17,18 has a respective frontmost border 17*a*,18*a* and respective rearmost border 17*b*,18*b*, as seen in the longitudinal direction L. In a flat unfolded configuration of the sanitary article 1, with the first and second fastening wings 15,16 being unfolded and extending outwardly of a respective side of the absorbent core 4 as the sanitary article 1 is illustrated in FIG. 1, the rearmost point 20*a* of the shaping element 20 is arranged in an area of the absorbent core 4 extending between a transverse extension of the frontmost border 17*a*,18*a* of the first and/or the second adhesive region 17,18, as seen in the longitudinal direction L, and the maximum width $W_{mh}$ of the head portion 12.

Each of the first and the second adhesive regions 17,18 provided on the first and second fastening wing 15,16 has a portion with a greater width and a portion with a smaller width, as measured in the transverse direction T. In FIG. 1 the respective adhesive regions 17,18 each comprises two rectangular portions, the adhesive regions 17,18 being reverse mirror-images of each other.

In FIG. 1, the absorbent core 4, is in the rear portion 11 of the sanitary article 1, divided along a longitudinal centerline $L_c$ of the absorbent core 4 into a first core leg portion 4*a* and a second core leg portion 4*b*. The absorbent core 4 is furthermore provided with a rear shaping element 22 in the rear portion 11 of the sanitary article 1, the rear shaping element 22 comprising a first and a second leg section 23,24 converging towards the longitudinal centerline $L_c$ of the absorbent core 4. The leg sections 23,24 are arranged to point towards the transverse rear edge 8 of the sanitary article 1 and here constitute of a low-density area. The leg sections 23,24 of the rear shaping element 22 converge into a converging low-density area extending along the longitudinal centreline $L_c$ of the sanitary article 1. The converging low-density area may comprise a density gradient with the lowest density in the area coinciding with the longitudinal centreline $L_c$ and a higher density at each side of this area. Each of the first and the second leg sections 23,24 has a respective first and second frontmost end point 23*a*,24*a* and each of the first and the second frontmost end points 23*a*,24*a* of the respective first and second leg sections 23,24 is arranged rearwardly of the first and/or second rearmost border 17*b*,18*b* of the first and/or the second adhesive regions 17,18. Since the adhesive regions 17,18 restrict the absorbent core 4 from bending and shaping in an area of the absorbent core 4 being aligned with the adhesive regions 17,18 as seen in the longitudinal direction L, the fact that the each of the first and the second frontmost end points 23*a*,24*a* of the respective first and second leg sections 23,24 is arranged rearwardly of the first and/or second rearmost border 17*b*,18*b* of the first and/or the second adhesive regions 17,18 allows the absorbent core 4 to benefit from the shaping effect of the rear shaping element 22.

Figure 2:
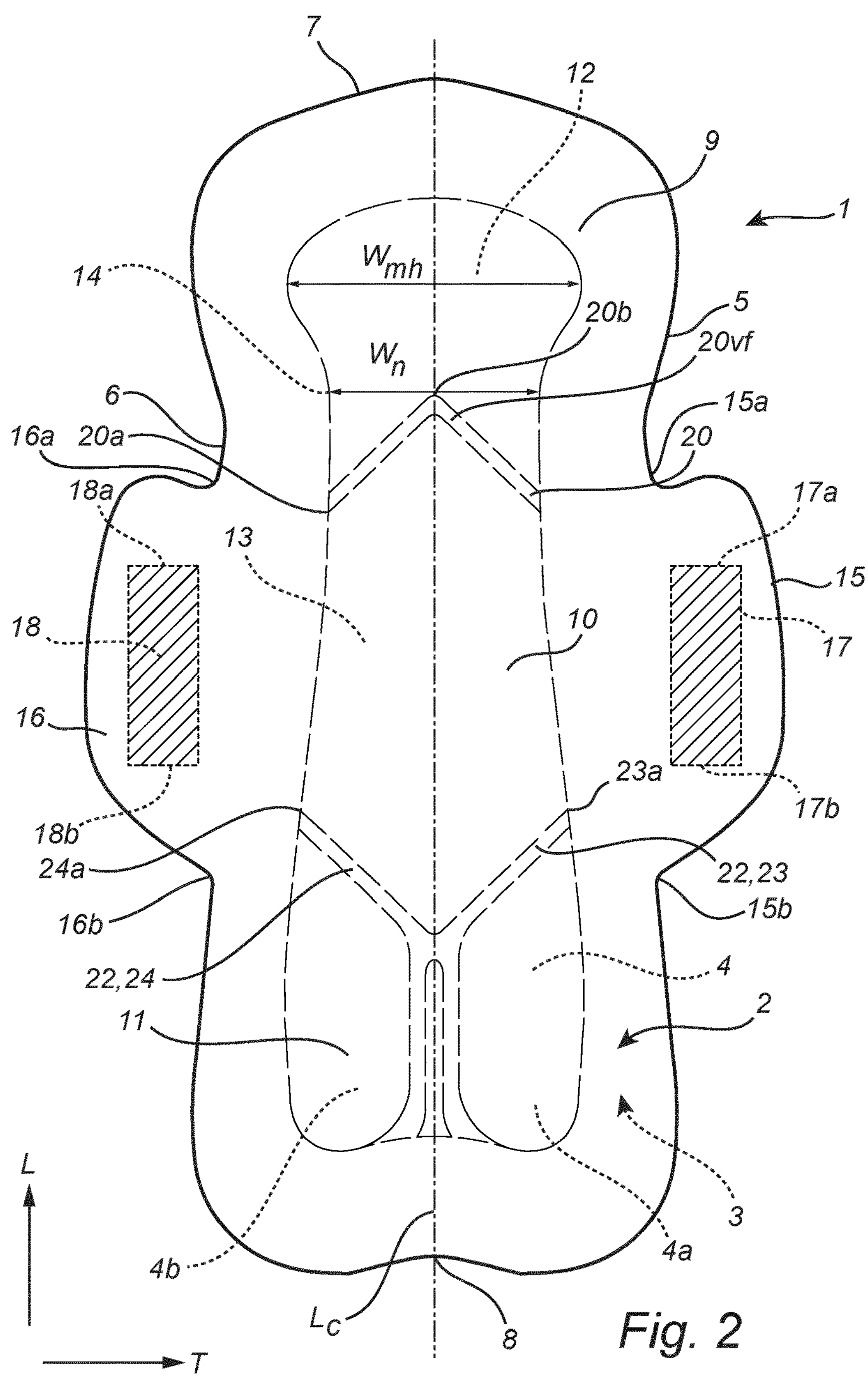
FIG. 2 illustrates an alternative sanitary article according to the present disclosure.

FIG. 2 illustrates a sanitary article 1 according to the present disclosure. The same reference signs as in FIG. 1 are used to denote the same or similar features. The sanitary article 1 comprising a topsheet 2, a backsheet 3 and an absorbent core 4 arranged between the topsheet 2 and the backsheet 3, the absorbent core 4 being similar to the absorbent core illustrated in FIG. 1. The sanitary article 1 may furthermore comprise an acquisition layer (not shown) arranged between the topsheet 2 and the absorbent core 4, as described in FIG. 1. The sanitary article 1 comprises fastening wings 15,16 which are asymmetric as seen along any transverse axis extending in the transverse direction T. The sanitary article 1 differs from the sanitary article 1 illustrated in FIG. 1 in that the fastening wings 15,16 are symmetrical with respect to each other as seen along any longitudinal axis extending in the longitudinal direction L.

The first fastening wing 15 has a first adhesive region 17 on a garment facing side thereof and the second fastening wing 16 has a second adhesive region 18 on a garment facing side thereof. Each of the first and the second adhesive regions 17,18 has a respective frontmost border 17*a*,18*a* and a respective rearmost border 17*b*,18*b*, as seen in the longitudinal direction L. In a flat unfolded configuration of the sanitary article 1, with the first and second fastening wings 15,16 being unfolded and extending outwardly of a respective side of the absorbent core 4 as the sanitary article 1 is illustrated in FIG. 1, the rearmost point 20*a* of the shaping element 20 is arranged in an area of the absorbent core 4 extending between a transverse extension of the frontmost border 17*a*,18*a* of the first and the second adhesive regions 17,18, as seen in the longitudinal direction L, and the maximum width $w_{mh}$ of the head portion 12.

Figure 3:
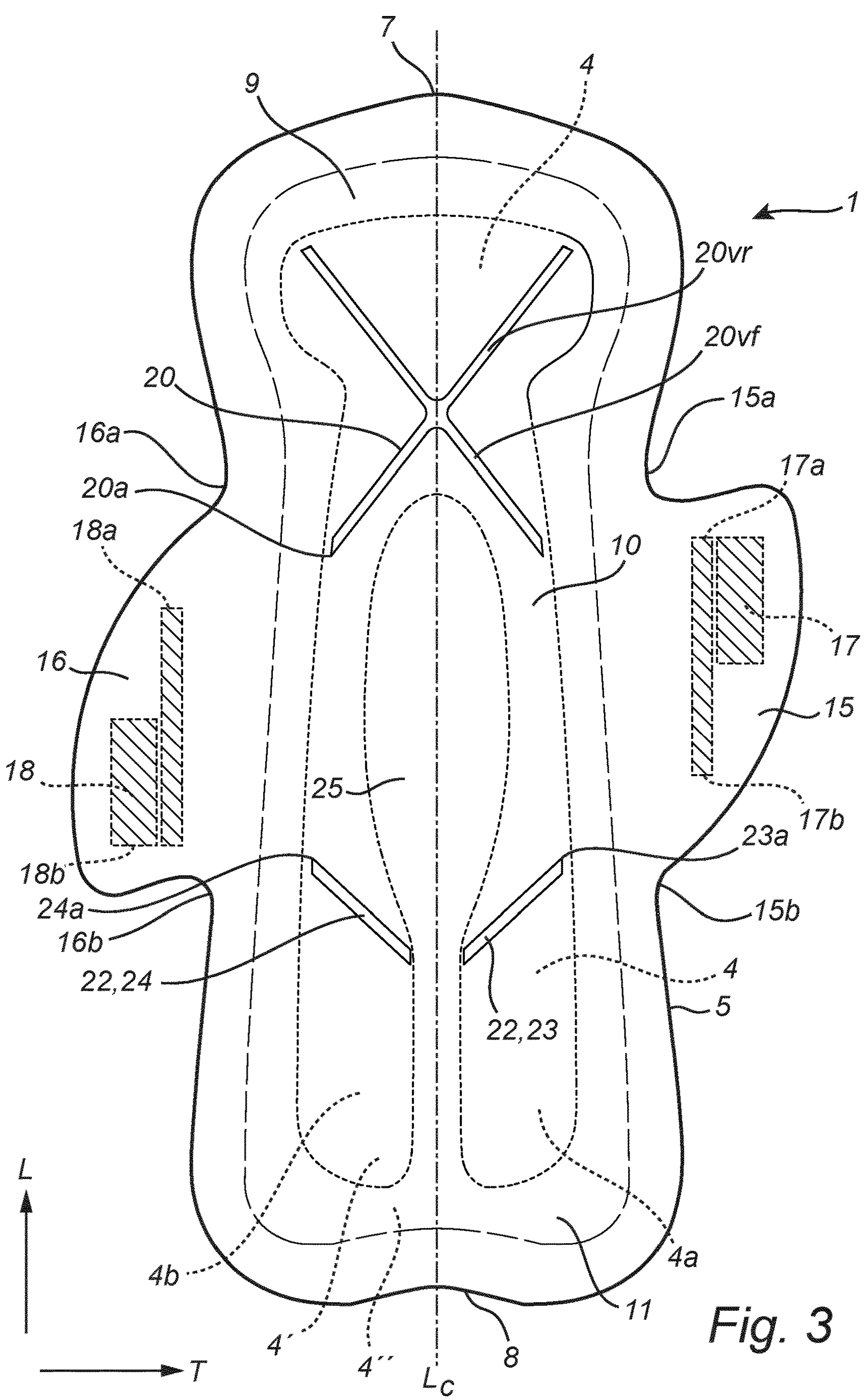
FIG. 3 illustrates a further sanitary article according to the present disclosure.

FIG. 3 illustrates a sanitary article 1 according to the present disclosure. The same reference signs as in FIG. 1 and FIG. 2 are used to denote the same or similar features. The sanitary article 1 comprising a topsheet 2, a backsheet 3 and an absorbent core 4 arranged between the topsheet 2 and the backsheet 3. The sanitary article 1 may furthermore comprise an acquisition layer (not shown) arranged between the topsheet 2 and the absorbent core 4, as described in FIG. 1.

The sanitary article 1 has an extension in a longitudinal direction L and in a transverse direction T. The sanitary article 1 is delimited by first and second longitudinal side edges 5,6 extending in the longitudinal direction L and front and rear transverse side edges 7,8 extending in the transverse direction T. The sanitary article comprises in a front portion 9, a crotch portion 10 and a rear portion 11, as seen in the longitudinal direction L. The absorbent core 4 comprises a head portion 12, a body portion 13 and a neck portion 14, the neck portion 14 forming a transitional region between the head portion 12 and the body portion 13. The head portion 12 is positioned in the front portion 9 of the sanitary article 1 and the body portion 13 is positioned in the crotch portion 10 and in the rear portion 11 of the sanitary article 1. A transverse width $w_n$ of the absorbent core 4 at the neck portion 14 is smaller than a maximum transverse width of the absorbent core 4 in the head portion 12 and in the body portion 13. The absorbent core 4 is provided with a shaping element 20 in the front portion 9 of the sanitary article 1. The shaping element may be a compressed groove, a channel, or a low-density region, promoting folding or shaping of the sanitary article 1. In FIG. 3, the shaping element 20 is a X-shaped embossing with a crossing-point being aligned with the neck portion 14 of the absorbent core 4. The X-shaped embossing has a rearmost point 20*a*, as seen in the longitudinal direction L.

The sanitary article 1 has a first fastening wing 15 extending along the first longitudinal side edge 5 between a first wing front junction 15*a* and a first wing rear junction 15*b* and a second fastening wing 16 extending along the second longitudinal side edge 6 between a second wing front junction 16*a* and a second wing rear junction 16*b*.

The first and second fastening wings 15,16 of the sanitary article 1 according to FIG. 3 are asymmetrical with respect to any transverse axis extending in the transverse direction T and with respect to each other as seen along any longitudinal axis extending in the longitudinal direction L.

The first fastening wing 15 has a first adhesive region 17 on a garment facing side thereof and the second fastening wing 16 has a second adhesive region 18 on a garment facing side thereof. Each of the first and the second adhesive regions 17,18 has a respective frontmost border 17*a*,18*a* and a respective rearmost border 17*b*18*b*, as seen in the longitudinal direction L. In a flat unfolded configuration of the sanitary article 1, with the first and second fastening wings 15,16 being unfolded and extending outwardly of a respective side of the absorbent core 4 as the sanitary article 1 is illustrated in FIG. 3, the rearmost point 20*a* of the X-shaped embossing is arranged in an area of the absorbent core 4 extending between a transverse extension of the frontmost border 17*a*,18*a* of the first and/or the second adhesive region 17,18, as seen in the longitudinal direction L, and and the maximum width $W_{mh}$ of the head portion 12. When the fastening wings 15,16 are asymmetrical with respect to any transverse axis extending in the transverse direction T and with respect to each other as seen along any longitudinal axis extending in the longitudinal direction L, the rearmost point 20*a* of the shaping element 20 may be arranged in an area of the absorbent core 4 extending between only one of the frontmost border 17*a*,18*a* of the first and the second adhesive regions 17,18.

Each of the first and the second adhesive regions 17,18 provided on the first and second fastening wing 15,16 has a respective portion with a greater width and a respective portion with a smaller width, as measured in the transverse direction T. In FIG. 3 the respective adhesive regions 17,18 each comprises two rectangular portions, the adhesive regions 17,18 being reverse mirror-images of each other.

In FIG. 3, in a rear portion 11 of the sanitary article 1, the absorbent core 4 is divided along a longitudinal centerline $L_c$ of the absorbent core 4 into a first core leg portion 4*a* and a second core leg portion 4*b*. The absorbent core 4 is provided with a central low-density area 25 being arranged in the crotch portion 10 of the sanitary article 1. The absorbent core 4 comprises a first absorbent core area 4' and a second absorbent core area 4", wherein the first absorbent core area 4' has a higher density than the second absorbent core area 4". In FIG. 3, the first absorbent core area 4' comprises the first core leg portion 4*a* and the second core leg portion 4*b*. The first absorbent core area 4' may be formed by compressing the area, such as by calendering or embossing. The embossing may for example be in the form of a pattern of embossed dots. The first absorbent core area 4' may for example have 20%, 30% or 40% higher density than the second absorbent core area 4".

The absorbent core 4 is furthermore provided with a rear shaping element 22 in the rear portion 11 of the sanitary article 1, the rear shaping element 22 comprising a first and a second leg section 23,24 converging towards a longitudinal centerline $L_c$ of the absorbent core 4. The first leg section 23 is arranged on the first core leg portion 4*a* and the second leg section 24 is arranged on the second core leg portion 4*b*. The leg sections 23,24 are arranged to point towards the transverse rear edge 8 of the sanitary article 1. The rear shaping element 22 is in FIG. 3 an embossing provided in both the topsheet 2 and the first layer 4' of the absorbent core 4. The rear shaping element 22 may alternatively be provided as an embossing in only the absorbent core 4 or it may be a non-compressed channel or low-density region, facilitating folding and shaping of the sanitary article 1 in the rear portion 11 of the sanitary article 1. Each of the first and the second leg sections 23,24 has a respective first and second frontmost end point 23*a*,24*a* and each of the first and the second frontmost end points 23*a*,24*a* of the respective first and second leg sections is arranged rearwardly of the first and second rearmost border 17*b*,18*b* of the first and the second adhesive regions 17,18.

Figure 4:
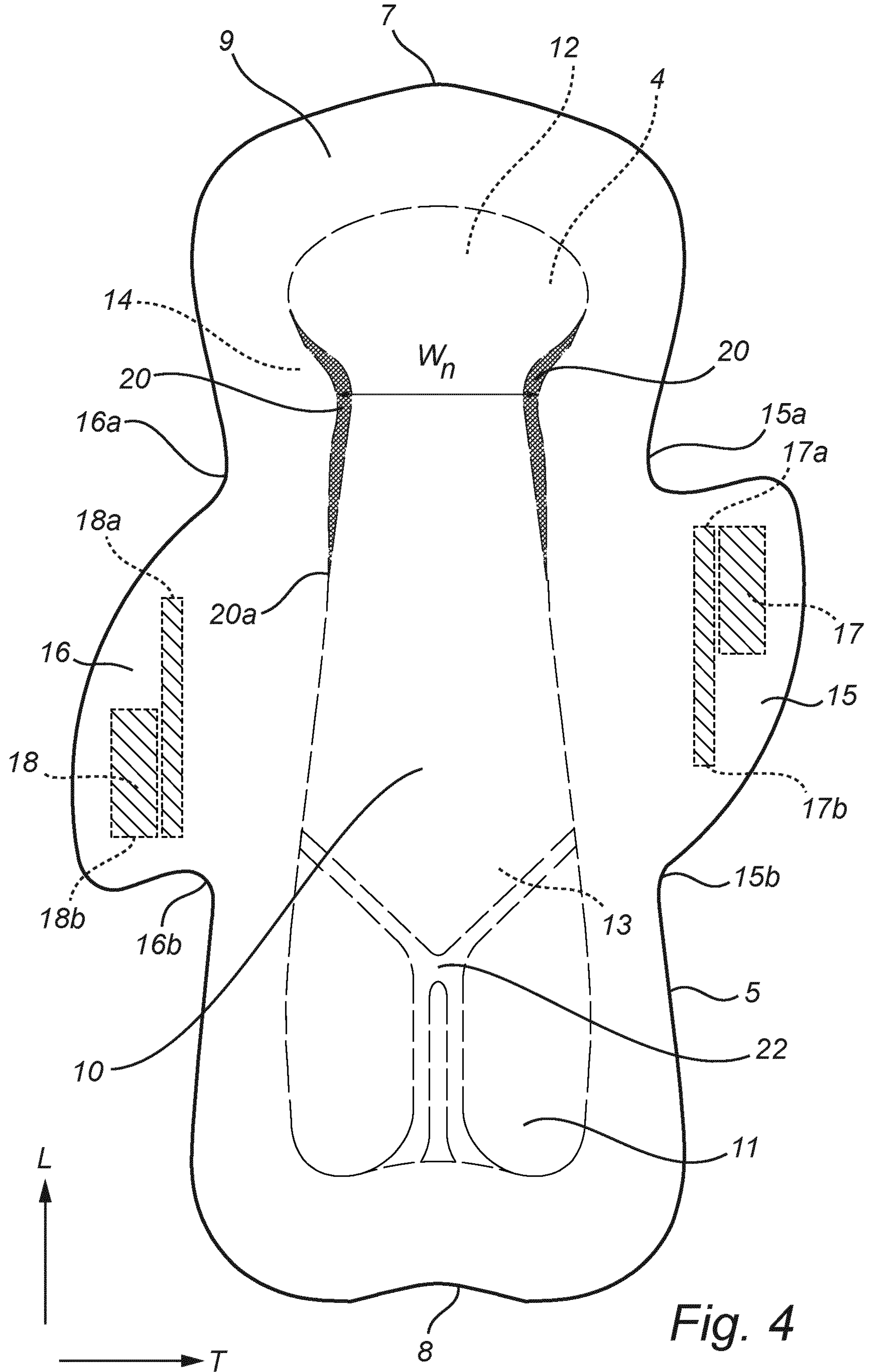
FIG. 4 illustrates a sanitary article according to the present disclosure.

FIG. 4 illustrates a sanitary article 1 according to the present disclosure. The same reference signs as in FIGS. 1-3 are used to denote the same or similar features. The sanitary article 1 comprises a topsheet 2, a backsheet 3 and an absorbent core 4 arranged between the topsheet 2 and the backsheet 3.

The sanitary article 1 has an extension in a longitudinal direction L and in a transverse direction T. The sanitary article 1 is delimited by first and second longitudinal side edges 5,6 extending in the longitudinal direction L and front and rear transverse side edges 7,8 extending in the transverse direction T. The sanitary article is made up of a front portion 9, a crotch portion 10 and a rear portion 11, as seen in the longitudinal direction L. The absorbent core 4 comprises a head portion 12, a body portion 13 and a neck portion 14, the neck portion 14 forming a transitional region between the head portion 12 and the body portion 13.

The head portion is positioned in the front portion 9 of the sanitary article 1 and the body portion 13 is positioned in the crotch portion 10 and in the rear portion 11 of the sanitary article 1. A transverse width $W_n$ of the absorbent core 4 at the neck portion 14 is smaller than a maximum transverse width $W_{mh}$ of the absorbent core 4 in the head portion 12 and in the body portion 13.

The sanitary article 1 in FIG. 4 is provided with a shaping element 20 in the form of a low-density region arranged along a respective first and second longitudinal edge region of the absorbent core 4 at the neck portion 14. The low-density region may for example have a density being at least 50% lower than an adjacent region of the absorbent core 4 or a density being at least 35% lower than an adjacent region of the absorbent core 4, optionally between 50% and 85% lower than an adjacent region of the absorbent core 4. The shaping element 20 may alternatively be a compressed region arranged along a respective first and second longitudinal edge region of the absorbent core 4 at the neck portion 14.

The sanitary article 1 has a first fastening wing 15 extending along the first longitudinal side edge 5 between a first wing front junction 15*a* and a first wing rear junction 15*b* and a second fastening wing 16 extending along the second longitudinal side edge 6 between a second wing front junction 16*a* and a second wing rear junction 16*b*.

The first and second fastening wings 15,16 of the sanitary article 1 according to FIG. 4 are asymmetrical with respect to any transverse axis extending in the transverse direction T and with respect to each other as seen along any longitudinal axis extending in the longitudinal direction L.

The first fastening wing 15 has a first adhesive region 17 on a garment facing side thereof and the second fastening wing 16 having a second adhesive region 18 on a garment facing side thereof. Each of the first and the second adhesive regions 17,18 has a respective frontmost border 17*a*,18*a*, as seen in the longitudinal direction L. In a flat unfolded configuration of the sanitary article 1, with the first and second fastening wings 15,16 being unfolded and extending outwardly of a respective side of the absorbent core 4, a rearmost point 20*a* of the shaping element 20 is arranged in an area of the absorbent core 4 extending between a transverse extension of the frontmost border 18*a* of the second adhesive region 18, as seen in the longitudinal direction L, to the maximum width $w_{mh}$ of the head portion 12.

Figure 5:
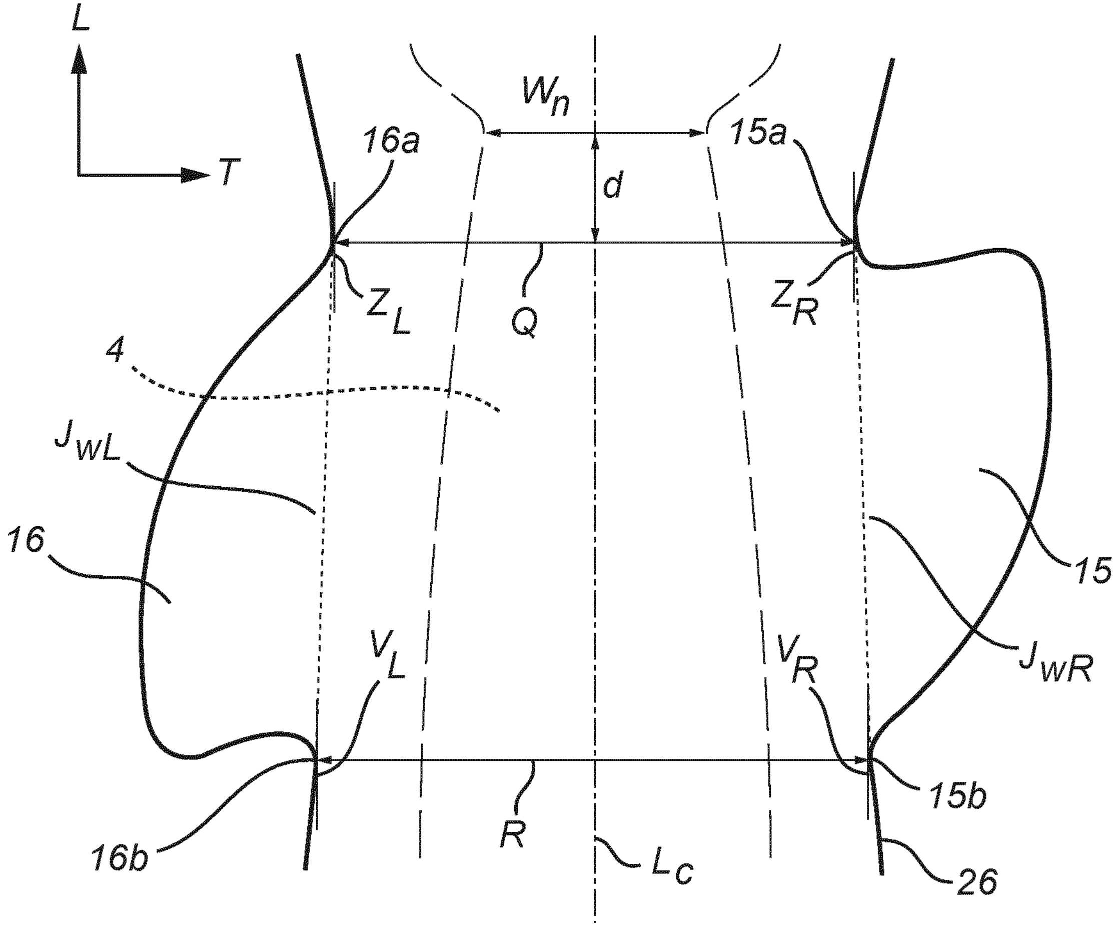
FIG. 5 illustrates a portion of a sanitary article with the definition of the front wing junctions and the rear wing junctions.

In the context of the present disclosure, the front wing junctions 15*a*,16*a* and the rear wing junctions 15*b*,16*b* are defined as follows and with reference to FIG. 5. In the crotch portion 10, a respective imaginary longitudinal straight line $Z_L$ and $Z_R$ is drawn, in the longitudinal direction L such that it touches an outer periphery 26 along a respective longitudinal side edge of the sanitary article 1 at the narrowest width Q in the transverse direction T of the sanitary article 1 forward of the first and second fastening wing 15,16. The intersection between an imaginary straight line $Z_R$ forward of the first fastening wing 15 and the outer periphery 26 is defined as the first front wing junction 15*a*, whereas the intersection between the imaginary straight line $Z_L$ forward of the second fastening wing 19 and the outer periphery 26 is defined as the second front wing junction 16*a*. In embodiments where the respective imaginary straight line $Z_R$,$Z_L$ coincides with the longitudinal side edges of the sanitary article 1 (e.g. because the longitudinal side edges of the sanitary article consist of straight lines), the front wing junctions 15*a* and 16*a* are defined as the point located on the section of the imaginary straight line coinciding with the outer periphery, being most closely located in the forward direction to the wing of the sanitary article.

As disclosed herein, the first wing front junction 15*a* and the second wing front junction 16*a* may be align with the neck portion 14 (see FIG. 1) of the absorbent core 4, or arranged with a distance d of not more than 30 mm rearwardly, or not more than 15 mm rearwardly, from the neck portion as measured in the longitudinal direction L. Alternatively, the front wing junction 15*a* and/or the second wing front junction 16*a* may be aligned with the neck portion 14 of the absorbent core 4, as seen in the longitudinal direction L The rear wing junctions 15*b*, 16*b* are defined by drawing an imaginary longitudinal straight line $V_{L,R}$ such that it touches the outer periphery 26 at the narrowest width R in the transverse direction of the sanitary article 1 rearward of the first and second wing 15,16. The intersection between the imaginary straight line $V_L$ in the longitudinal direction L of the sanitary article 1 and rearward of the second wing 16 and the outer periphery 26 is defined as the second rear wing junction 16*b*, whereas the intersection between the imaginary straight line $V_R$ rearward of the first wing 15 and the outer periphery 26 is defined as the first rear wing junction 15*b*. In embodiments where the imaginary straight line $V_L$, $V_R$ coincides with the longitudinal side edges of the sanitary article 1 (e.g. because the longitudinal side edges of the outer periphery consist of straight lines), the rear wing junctions 15*b* and 16*b* are defined as the point located on the section of the imaginary straight line coinciding with the outer periphery 26, being most closely located in the rearward direction to the wing of the sanitary article, i.e. the wing deflection point. As shown in FIG. 5, an imaginary second wing junction line $J_{wL}$ connects the second front wing junction 16*a* with the second rear wing junction 16*b*, while an imaginary first wing junction line $J_{wR}$ connects the first front wing junction 15*a* with the first rear wing junction 15*b*. In the context of this application, the first and second wing junction lines $J_{wR}$ and $J_{wL}$ correspond to the wing length. In a sanitary napkin of the type shown, the rear wing junctions 15*b*,16*b* are spaced further outboard of a longitudinal centerline $L_c$ of the sanitary article 1 as compared to the front wing junctions 15*a*, 16*a*. Consequently, the first and second wing junction lines $J_{wR}$ and $J_{wL}$ are not parallel to the longitudinal centerline $L_c$. However, the rear wing junctions 15*b*,16*b* may also be spaced such that the transverse distance between the rear wing junctions 15*b*,16*b* and the longitudinal centerline $L_c$ is equal to the transverse distance between the front wing junctions 15*a*,16*a* and the longitudinal centerline $L_c$. In such an embodiment, the first and second wing junction lines $J_{wR}$ and $J_{wL}$ are parallel to the longitudinal centerline $L_c$. In a sanitary napkin of the type shown, the first and second wing junction lines $J_{wR}$ and $J_{wL}$ have a length of 50-110 mm, preferably between 75-100 mm, and most preferably between 85-95 mm.

The invention claimed is:

1. A sanitary article comprising:

a topsheet;

a backsheet; and an absorbent core arranged between the topsheet and the backsheet, wherein the sanitary article extends in a longitudinal direction and in a transverse direction, wherein the sanitary article has first and second longitudinal side edges extending in the longitudinal direction and front and rear transverse side edges extending in the transverse direction, wherein the sanitary article is divided in a front portion, a crotch portion and a rear portion along the longitudinal direction, wherein the absorbent core comprises a head portion, a body portion, and a neck portion, wherein the neck portion forms a transitional region between the head portion and the body portion, wherein the head portion is positioned in the front portion of the sanitary article and the body portion is positioned in the crotch portion and in the rear portion of the sanitary article, wherein a transverse width of the absorbent core at the neck portion is smaller than a maximum transverse width of the absorbent core in the head portion and in the body portion, wherein the absorbent core in the front portion of the sanitary article is provided with a shaping element, promoting folding or shaping of the sanitary article, wherein the shaping element is at least one of a compressed groove, a channel, or a low density region, wherein the shaping element comprises a rearmost point along the longitudinal direction of the sanitary article, wherein the sanitary article has a first fastening wing extending along the first longitudinal side edge between a first wing front junction and a first wing rear junction and a second fastening wing extending along the second longitudinal side edge between a second wing front junction and a second wing rear junction, wherein the first fastening wing has a first adhesive region on a garment facing side thereof, wherein the second fastening wing has a second adhesive region on a garment facing side thereof, wherein each of the first adhesive region and the second adhesive region has a respective frontmost border along the longitudinal direction and a respective rearmost border along the longitudinal direction, wherein the sanitary article has a flat unfolded configuration in which the first and second fastening wings are unfolded and extend outwardly of a respective side of the absorbent core, wherein, in the flat unfolded configuration, the rearmost point of the shaping element is arranged in an area of the absorbent core extending between a transverse extension of the frontmost border of the first adhesive region and/or the second adhesive region along the longitudinal direction to a maximum width portion of the head portion, and wherein the absorbent core has no shaping element between the rearmost point of the shaping element and a transverse extension of the rearmost border of the first adhesive region and/or the second adhesive region along the longitudinal direction.

2. The sanitary article according to claim 1, wherein a portion of the shaping element coincides with the neck portion of the absorbent core along the longitudinal direction, or is arranged not more than 15 mm from the neck portion, as measured in the longitudinal direction.

3. The sanitary article according to claim 1, wherein the first wing front junction and/or the second wing front junction are/is aligned with the neck portion of the absorbent core along the longitudinal direction, or are/is arranged not more than 15 mm rearwardly from the neck portion as measured in the longitudinal direction.

4. The sanitary article according to claim 1, wherein the shaping element has a V-shaped section pointing towards the transverse front edge of the sanitary article and/or a V-shaped section pointing towards the transverse rear edge of the sanitary article and/or a first and a second compressed or low-density region arranged along a respective first and second longitudinal edge region of the absorbent core at the neck portion.

5. The sanitary article according to claim 1, wherein the shaping element is either a compressed groove or a channel with a depth corresponding to 50% or more of a no-load thickness of the absorbent core, or a low-density region in which the low-density region has a density corresponding to 50% or less of the density of the absorbent core, the no-load thickness or the density of the absorbent core being measured in an area of the absorbent core adjacent to the shaping element.

6. The sanitary article according to claim 1 wherein the shaping element extends to a first and a second longitudinal edge region of the absorbent core.

7. The sanitary article according to claim 1, wherein the shaping element is symmetrical about a longitudinal centerline of the absorbent core.

8. The sanitary article according to claim 1, wherein the first and second fastening wings are asymmetrical with respect to any transverse axis extending in the transverse direction.

9. The sanitary article according to claim 1, wherein the first and second fastening wings are asymmetrical with respect to each other as seen along any longitudinal axis extending in the longitudinal direction.

10. The sanitary article according to claim 8, wherein each of the first and the second adhesive regions has a respective portion with a greater width and a respective portion with a smaller width, as measured in the transverse direction.

11. The sanitary article according to claim 10, wherein the first and the second adhesive region are reverse mirror images of each other.

12. The sanitary article according to claim 1, wherein a frontmost point of the shaping element is aligned with the neck portion of the absorbent core along the transverse direction.

13. The sanitary article according to claim 1, wherein the body portion of the absorbent core in the rear portion of the sanitary article is divided along a longitudinal centerline of the absorbent core into a first core leg portion and a second core leg portion.

14. The sanitary article according to claim 1, wherein the absorbent core is provided with a central low-density area, the central low-density area being arranged in the crotch portion of the sanitary article.

15. The sanitary article according to claim 1, wherein the absorbent core is provided with a rear shaping element comprising a first leg section and a second leg section, wherein the first and the second leg sections converge towards a longitudinal centerline of the absorbent core and point towards the transverse rear edge of the sanitary article, wherein each of the first and the second leg sections has a respective first and second frontmost end point, and wherein each of the first and the second frontmost end points of the respective first and second leg sections is aligned with or arranged rearwardly of the rearmost borders of the first and the second adhesive regions.

16. The sanitary article according to claim 1, wherein a frontmost portion of the shaping element overlaps the neck portion.

17. The sanitary article according to claim 1, wherein one of the first adhesive region and the second adhesive region does not overlap the shaping element in the transverse direction.

18. The sanitary article according to claim 1, wherein both the first adhesive region and the second adhesive region do not overlap the shaping element in the transverse direction.

19. The sanitary article according to claim 1, wherein a frontmost portion of the first adhesive region is forward of a frontmost portion of the second adhesive region.

20. The sanitary article according to claim 1, wherein the shaping element has a V-shaped section pointing towards the transverse front edge of the sanitary article.

* * * * *